US00PP25532P2

(12) United States Plant Patent
Finn

(10) Patent No.: US PP25,532 P2
(45) Date of Patent: May 12, 2015

(54) BLACKBERRY PLANT NAMED 'COLUMBIA STAR'

(50) Latin Name: ***Rubus* subg. *Rubus* Watson**
Varietal Denomination: Columbia Star

(71) Applicant: The United States of America, as represented by the Secretary of Agriculture, Washington, DC (US)

(72) Inventor: Chad E Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 100 days.

(21) Appl. No.: 13/815,074

(22) Filed: Jan. 29, 2013

(51) Int. Cl.
*A01H 5/00* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

PP17,983 P2 9/2007 Cabrera Avalos
PP22,002 P2 7/2011 Sills et al.

*Primary Examiner* — Anne Grunberg
(74) *Attorney, Agent, or Firm* — Gail E. Poulos; John D. Fado; Lesley Shaw

(57) ABSTRACT

A new and distinct blackberry cultivar that originated from seed produced from a cross between the female blackberry plant 'NZ 9629-1' (unpatented) and the male parent blackberry plant 'ORUS 1350-2' (unpatented). This new blackberry cultivar can be distinguished by its high yields of large, very uniformly shaped berries with very good flavor, sweetness, and fruit chemistry as characterized by soluble solids, pH, and titratable acidity that make them well suited for processing. The new and distinct blackberry variety has fruit that are borne on vigorous, completely thornless plants and can be harvested by machine.

5 Drawing Sheets

Latin name of the genus and species of the plant claimed: 'COLUMBIA STAR' is a blackberry plant that is *Rubus* subg. *Rubus* Watson.

Variety denomination:

The new blackberry plant claimed is of the variety denominated 'Columbia Star' *Rubus* subg. *Rubus* Watson.

BACKGROUND OF THE INVENTION

The present invention relates to a new and distinct blackberry cultivar designated 'Columbia Star' and botanically known as *Rubus* subg. *Rubus* Watson. This new blackberry cultivar was discovered in Corvallis, Oreg. in July 2008 and originated from a cross between the female blackberry plant 'NZ 9629-1' (unpatented) and the male parent blackberry plant 'ORUS 1350-2' (unpatented). 'Columbia Star's spinelessness is derived from 'Lincoln Logan' (unpatented) that can be found as a parent four and five generations back in 'Columbia Star's pedigree. The original seedling of the new cultivar was asexually propagated at a nursery in Benton County, Oreg. The new cultivar was established in vitro from a cane cutting and microcuttings have been taken and rooted from this sort of culture. The present invention has been found to be stable and reproduce true to type through successive asexual propagations.

BRIEF DESCRIPTION OF THE PHOTOGRAPHS

This new blackberry plant is illustrated by the accompanying photographs that show the fruit of the plant and machine harvested fruit, as well as canes and entire plants; the colors shown are as true as can be reasonably obtained by conventional photographic procedures.

Figure 1:
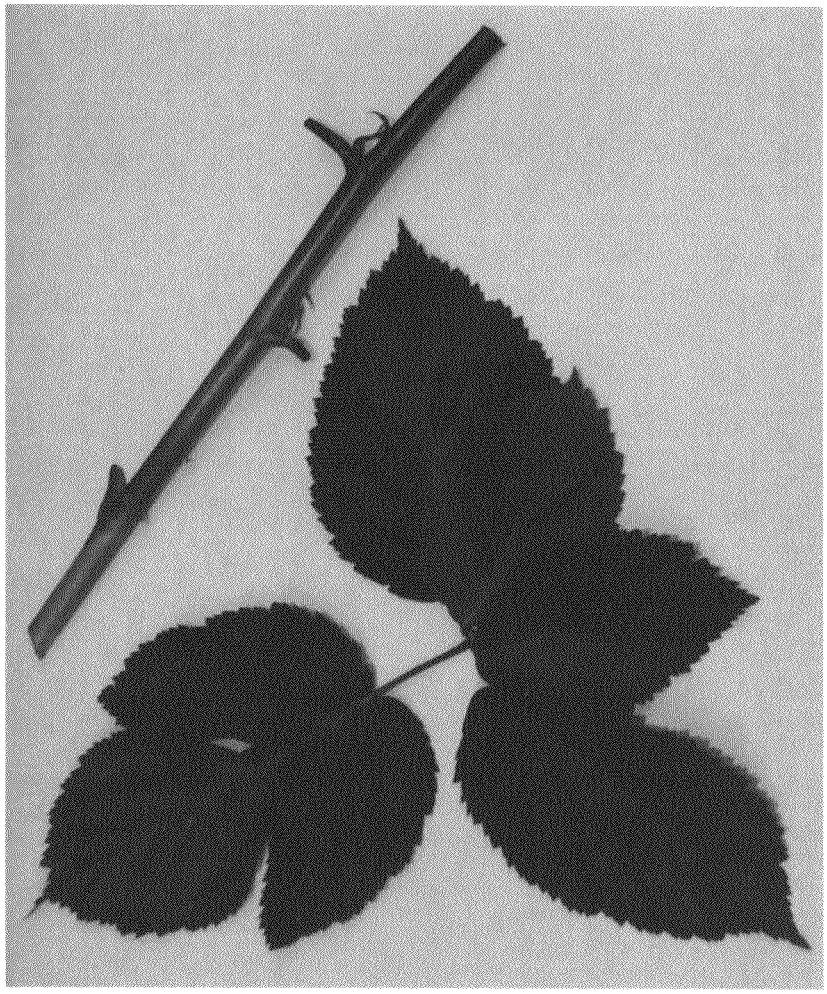

FIG. 1. shows a section of a spineless primocane and a leaf.

Figure 2:
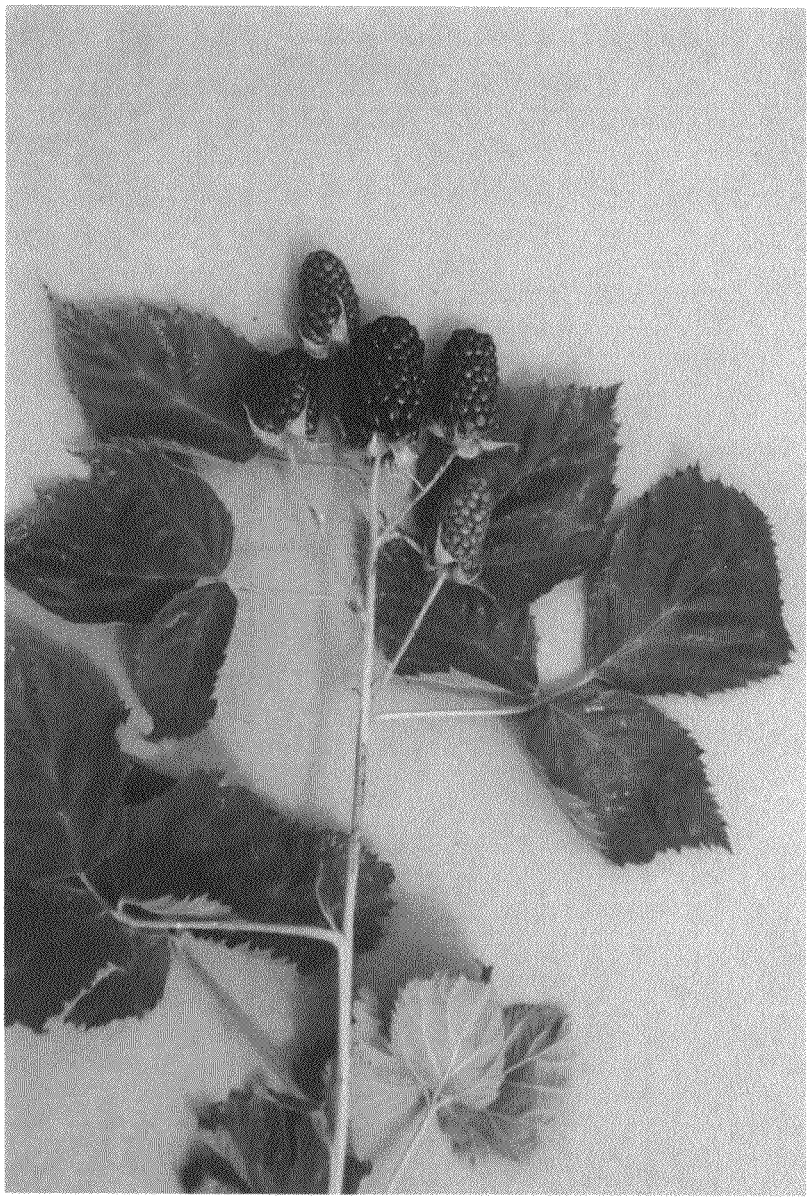

FIG. 2. shows a fruiting lateral with typical leaves.

Figure 3:
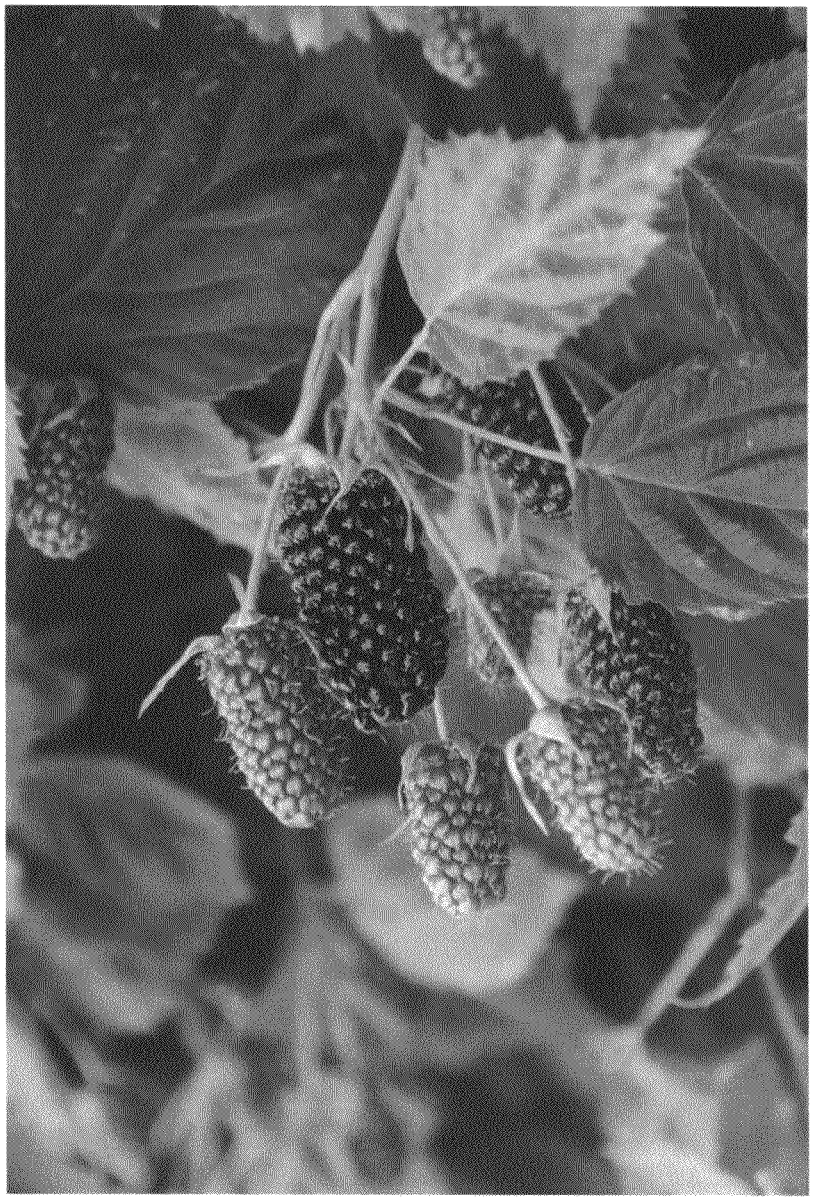

FIG. 3. shows typical fruit in a fruit cluster in the field.

Figure 4:
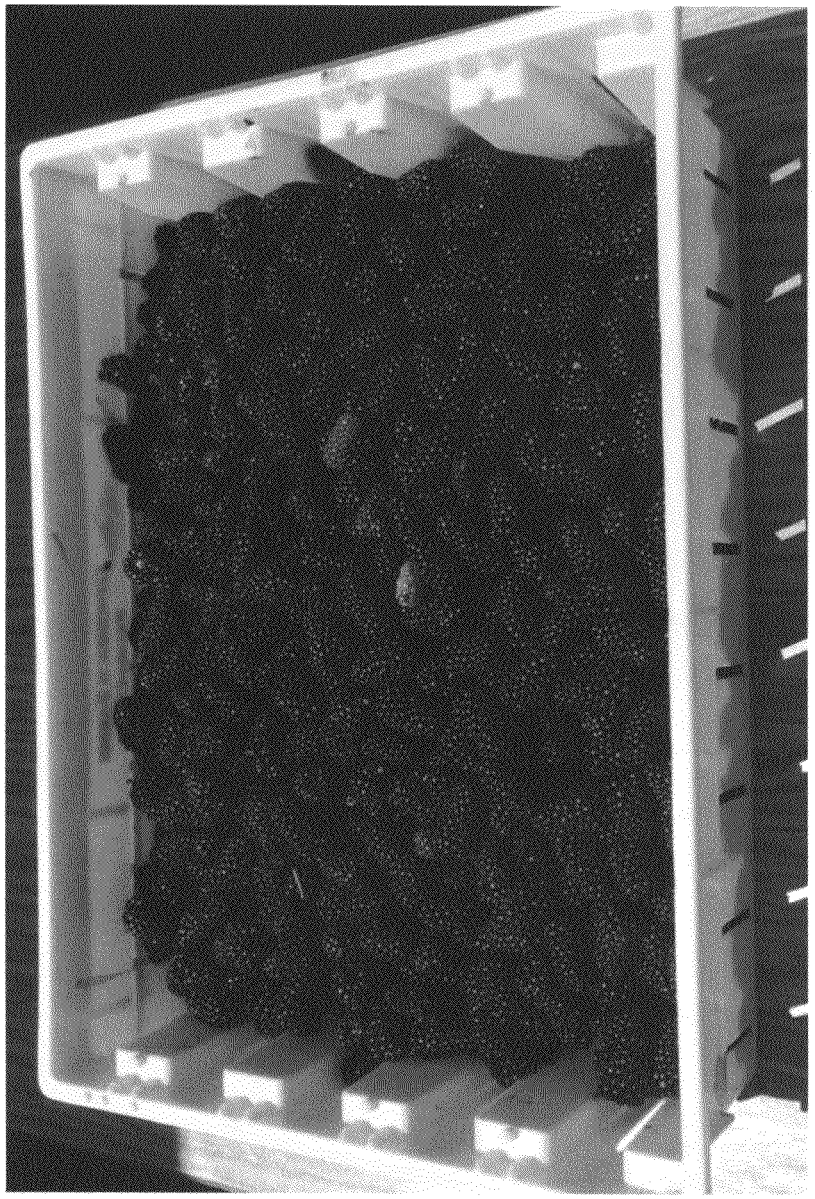

FIG. 4. shows machine harvested fruit.

Figure 5:
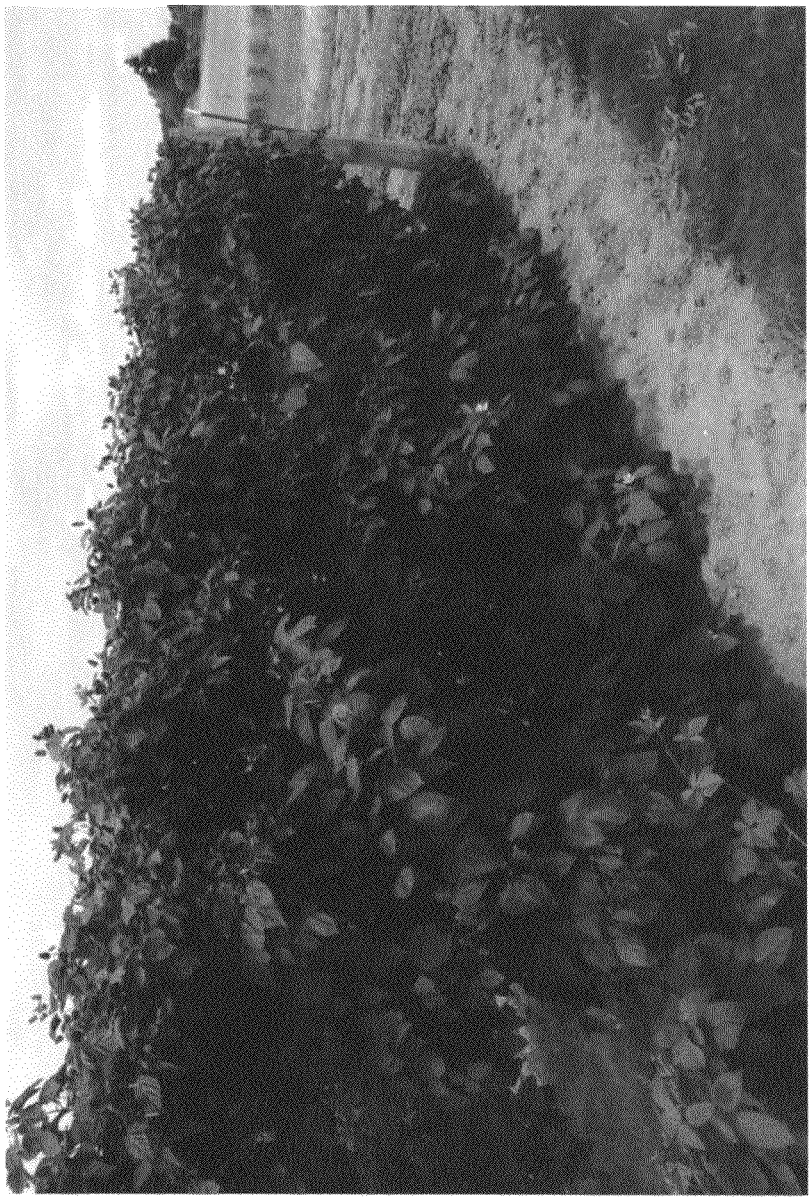

FIG. 5. shows an entire 5-year old plant.

DETAILED DESCRIPTION OF THE NEW CULTIVAR

The following description of 'Columbia Star' is based on observations taken from 2009 to 2012 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Columbia Star' has not been observed under all possible environmental conditions. Color terminology follows The Royal Horticultural Society Colour Chart. London (R.H.S.) ($5^{th}$ edition, 2007).

Table 1 shows plant characteristics of the new cultivar compared with plant characteristics of the blackberry plants 'Marion', (unpatented) and 'Black Diamond', (unpatented). Characteristics include plant vigor, presence of spines further than 0.6 m from the soil surface, presence of spines less than 0.6 m from the soil surface, weight of primary fruit, uniformity of berry shape, fruit firmness, fruit flavor, fruit soluble solids (%; in Brix), fruit pH, fruit titratable acidity (% as citric acid), and yield (actual kg•plt-1).

TABLE 1

| Characteristic | Columbia Star | Marion | Black Diamond |
|---|---|---|---|
| Plant vigor | High | High | Medium |
| Presence of spines further than 0.6 m from the soil surface | Absent | Numerous | Absent |
| Presence of spines less than 0.6 m from the soil surface | Absent | Numerous | Numerous |
| Weight of primary fruit | 7.96 g | 3.76 g | 6.92 g |
| Uniformity of berry shape | Excellent | Fair | Excellent |
| Fruit firmness | Very good | Poor | Good |
| Fruit flavor | Excellent | Excellent | Good |
| Fruit soluble solids (%; in Brix) | 12.80 | 12.28 | 10.47 |
| Fruit pH | 3.20 | 3.27 | 3.40 |
| Fruit titratable acidity (% as citric acid) | 15.76 | 14.75 | 12.02 |
| Yield (actual kg · plt-1) | 6.98 | 5.83 | 4.75 |

Table 2 shows plant characteristics of the new cultivar compared with plant characteristics of the blackberry plants 'Marion', (unpatented) and 'Black Diamond', (unpatented). Characteristics include plant vigor, growth habit, date of budbreak, timing of primocane emergence, primocane length on 14 Jun. 2012, and winter tolerance in Lynden, Wash. (48° 56' 48" N/122° 27' 2" W).

TABLE 2

| Characteristic | Columbia Star | Marion | Black Diamond |
|---|---|---|---|
| Plant vigor | High | High | Medium |
| Growth habit | Trailing | Trailing | Trailing |
| Date of budbreak | 27 Mar. 2012 | 27 Mar. 2012 | 27 Mar. 2012 |
| Timing of primocane emergence | Early to medium | Medium | Medium to late |
| Winter tolerance in Lynden, Washington (48° 56' 48" N/ 122° 27' 2" W) | Good-very good | Fair-good | very good |

Table 3 shows floricane and mature primocane characteristics of the new cultivar compared with floricane and mature primocane characteristics of the blackberry plants 'Marion', (unpatented) and 'Black Diamond', (unpatented). Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, and floricane length (range).

TABLE 3

| Characteristic | Columbia Star | Marion | Black Diamond |
|---|---|---|---|
| Diameter at base | 0.84 cm | 1.13 cm | 1.44 cm |
| Diameter at midpoint | 0.56 cm | 0.85 cm | 0.80 cm |
| Diameter at terminus | 0.31 cm | 0.27 cm | 0.55 cm |
| Internode length at base | 6.03 cm | 6.37 cm | 5.04 cm |
| Internode length at midpoint | 5.22 cm | 5.63 cm | 5.77 cm |
| Internode length at terminus | 3.81 cm | 5.99 cm | 4.90 cm |
| Presence of spines further than 0.6 m from the soil surface | Absent | Numerous | Absent |

TABLE 3-continued

| Characteristic | Columbia Star | Marion | Black Diamond |
|---|---|---|---|
| Presence of spines less than 0.6 m from the soil surface | Absent | Numerous | Numerous |
| Floricane color at base | 144A | 146B | 152A |
| Floricane color at midpoint | 146C | 146B | 152A |
| Floricane color at terminus | 144B | 152C | 152B |
| Floricane lateral length | Medium-long | Long | Short |
| Floricane lateral strength | Medium | Weak to medium | Strong |
| Primocane color at base | 144A | 138B-146D w/red (166A) streaking | 144A w/red (187A) streaking |
| Primocane color at midpoint | 144A | 143C-145A w/ red (166A) streaking | 146C w/red (187A) streaking |
| Primocane color at terminus | 144B | 146D | 144A, often streaked w/red (187A) |
| Floricane length (range) | 2.8-3.7 m | 4.9-5.8 m | 2.7-4.3 m |

Table 4 shows primocane foliage characteristics of the new cultivar compared with primocane foliage characteristics of the blackberry plants 'Marion', (unpatented) and 'Black Diamond', (unpatented). Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet: upper surface, pubescence on primocane leaflet: undersurface, primocane leaf color abaxial, primocane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, and stipule width.

TABLE 4

| Characteristic | Columbia Star | Marion | Black Diamond |
|---|---|---|---|
| Mature compound leaf width | 22.07 cm | 17.21 cm | 19.75 cm |
| Mature compound leaf length | 22.42 cm | 15.52 cm | 18.83 cm |
| Number of leaflets per primocane compound leaf | Usually 5 | Usually 3; sometimes 5 | Usually 5; ranges from 3-7 |
| Mature leaflet shape | Ovate | Ovate | Ovate to Cordate |
| Mature leaflet apex | Acute | Broadly acuminate/acute | Broadly acuminate |
| Mature leaflet base | Cordate | Rounded | Round to cordate |
| Mature terminal leaflet width | 8.70 cm | 8.22 cm | 7.43 cm |
| Mature terminal leaflet length | 11.68 cm | 10.07 cm | 8.83 cm |
| Mature first lateral leaflet width | 4.92 cm | 5.97 cm | 7.72 cm |
| Mature first lateral leaflet length | 7.30 cm | 8.37 cm | 10.07 cm |
| Leaflet margin | Double serrate | Serrate | Serrate |
| Leaflet serration teeth length | 0.42 cm | 0.18 cm | 0.24 cm |
| Leaflet serration teeth width at base | 1.07 cm | 0.34 cm | 0.40 cm |

TABLE 4-continued

| Characteristic | Columbia Star | Marion | Black Diamond |
|---|---|---|---|
| Spine presence on leaves | Absent | Long prickles on sides and back of petiole, petiolules, midveins; smaller prickles on lateral veins | Very short, soft spines on sides and back of petiole, petiolules, midveins and larger lateral veins |
| Pubescence on primocane leaflet: upper surface | Light | Medium to coarse | Sparse |
| Pubescence on primocane leaflet: undersurface | Light | Heavy, soft | Heavy, soft |
| Primocane leaf color abaxial | N137A | N137 | N137 |
| Primocane leaf color adaxial | 137B | 147B | 147B |
| Petiole length | 8.18 cm | 5.42 cm | 7.90 cm |
| Petiole color: upper surface | 144A | 146B-C | 146A & 146B, maturing to 177A |
| Petiole color: undersurface | 144B streaked with red 184A | 144B | 144B |
| Petiolule length: terminal leaflet | 2.83 cm | 2.12 cm | 4.43 cm |
| Petiolule length: first distal leaflet | 0.28 cm | 0.28 cm | 0.68 cm |
| Petiolule color: abaxial | 200B | 146B-146C | 146A & 146B |
| Petiolule color: adaxial | 144B | 144B | 144B |
| Stipule length | 2.20 cm | 1.39 cm | 0.90 cm |
| Stipule width | 0.20 cm | 0.31 cm | 0.23 cm |

Table 5 shows floricane foliage characteristics of the new cultivar compared with floricane foliage characteristics of the blackberry plants 'Marion', (unpatented) and 'Black Diamond', (unpatented). Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet: undersurface, floricane leaf color abaxial, floricane leaf color adaxial, petiole length, petiolule length: terminal leaflet, petiolule length: first distal leaflet, petiolule color: abaxial, petiolule color: adaxial, stipule length, and stipule width.

TABLE 5

| Characteristic | Columbia Star | Marion | Black Diamond |
|---|---|---|---|
| Mature compound leaf width | 16.70 cm | 13.52 cm | 11.57 cm |
| Mature compound leaf length | 16.07 cm | 12.32 cm | 11.68 cm |
| Number of leaflets per floricane compound leaf | Usually 3 | Usually 3; occasionally 1 | Usually 3; occasionally 1 or 5 |
| Mature leaflet shape | Ovate | Oval to ovate | Oval to ovate |
| Mature leaflet apex | Acute | Acute to broadly acuminate | Acute |
| Mature leaflet base | Rounded | acute to rounded | rounded to cordate |
| Mature terminal leaflet width | 7.27 cm | 6.55 cm | 6.18 cm |

TABLE 5-continued

| Characteristic | Columbia Star | Marion | Black Diamond |
|---|---|---|---|
| Mature terminal leaflet length | 11.47 cm | 8.00 cm | 8.28 cm |
| Mature first lateral leaflet width | 6.18 cm | 5.30 cm | 4.77 cm |
| Mature first lateral leaflet length | 9.07 cm | 7.67 cm | 6.57 cm |
| Leaflet margin | Double serrate | Serrate | Serrate |
| Leaflet serration teeth length | 0.29 cm | 0.29 cm | 0.27 cm |
| Leaflet serration teeth width at base | 0.48 cm | 0.81 cm | 0.64 cm |
| Pubescence on floricane leaflet: upper surface | Light | Light | None |
| Pubescence on floricane leaflet: undersurface | Light | Heavy | Medium |
| Floricane leaf color abaxial | N137A | 146A | 147A |
| Floricane leaf color adaxial | 137C | 148B | 147B |
| Petiole length | 7.07 cm | 4.67 cm | 4.43 cm |
| Petiolule length: terminal leaflet | 2.28 cm | 1.32 cm | 1.90 cm |
| Petiolule length: first distal leaflet | 0.30 cm | 0.33 cm | 0.23 cm |
| Petiolule color: abaxial | 145A | 146C | 146C |
| Petiolule color: adaxial | 185A & 145A | 144C | 144B |
| Stipule length | 1.36 cm | 0.964 cm | 0.25 cm |
| Stipule width | 0.12 cm | 0.19 cm | 0.04 cm |

Table 6 shows flower and flowering characteristics of the new cultivar compared with flower and flowering characteristics of the blackberry plants 'Marion', (unpatented) and 'Black Diamond', (unpatented). Flower and flowering characteristics include date 1st bloom, date full bloom, date last bloom, petal color, number of flowers per cluster, number of petals per flower, flower diameter, petal length, petal width, and number of sepals per flower.

TABLE 6

| Characteristic | Columbia Star | Marion | Black Diamond |
|---|---|---|---|
| Date 1st bloom | 7-May | 21-May | 14-May |
| Date full bloom | 15-May | 28-May | 21-May |
| Date last bloom | 17 June | 17 June | 14 June |
| Petal color | 155C | NN155D | NN155C |
| Number flowers per cluster | 3.50 | 8.00 | 9.17 |
| Number of petals per flower | 5.17 | 5.17 | 5.33 |
| Flower diameter | 3.23 cm | 6.14 cm | 2.51 cm |
| Petal length | 1.65 cm | 1.93 cm | 1.32 cm |
| Petal width | 0.96 cm | 1.21 cm | 1.00 cm |
| Number of sepals per flower | 5.83 | 5.50 | 5.83 |

Table 7 shows fruit and fruiting characteristics of the new cultivar compared with fruit and fruiting characteristics of the blackberry plants 'Marion', (unpatented) and 'Black Diamond', (unpatented). Fruit and fruiting characteristics include date 5% of fruit were ripe, date 50% of fruit were ripe, date 95% of fruit were ripe, weight of primary fruit, weight of secondary fruit, weight of tertiary fruit, diameter of primary fruit at equator, diameter of 2° fruit at equator, diameter of 3° fruit at equator, diameter of 1° fruit at poles: tip, diameter of 1° fruit at poles: base, diameter of 2° fruit at poles: tip, diameter of 2° fruit at poles: base, diameter of 3° fruit at poles:

tip, diameter of 3° fruit at poles: base, berry length primary fruit, berry length 2° fruit, berry length 3° fruit, ratio of primary fruit length to width, shape description, uniformity of berry shape, color when full ripe, number of drupelets per fruit, drupelet weight, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), and yield (actual kg•plt-1). Fruit is borne only on floricanes.

TABLE 7

| Characteristic | Columbia Star | Marion | Black Diamond |
|---|---|---|---|
| Date 5% of fruit were ripe | 7 July | 14 July | 7 July |
| Date 50% of fruit were ripe | 18 July | 21 July | 25 July |
| Date 95% of fruit were ripe | 1 August | 1 August | 4 August |
| Weight of primary fruit | 7.96 g | 3.76 g | 6.92 g |
| Weight of secondary fruit | 9.68 g | 4.21 g | 6.49 g |
| Weight of tertiary fruit | 8.02 g | 6.79 g | 6.44 g |
| Diameter of primary fruit at equator | 1.94 cm | 1.71 cm | 1.98 cm |
| Diameter of 2° fruit at equator | 1.98 cm | 1.80 cm | 1.96 cm |
| Diameter of 3° fruit at equator | 1.88 cm | 1.91 cm | 1.90 cm |
| Diameter of 1° fruit at poles: tip | 1.28 cm | 1.05 cm | 1.24 cm |
| Diameter of 1° fruit at poles: base | 1.68 cm | 1.63 cm | 1.82 cm |
| Diameter of 2° fruit at poles: tip | 1.25 cm | 1.04 cm | 1.12 cm |
| Diameter of 2° fruit at poles: base | 1.82 cm | 1.60 cm | 1.70 cm |
| Diameter of 3° fruit at poles: tip | 3.85 cm | 1.14 cm | 1.25 cm |
| Diameter of 3° fruit at poles: base | 1.73 cm | 1.79 cm | 1.76 cm |
| Berry length primary fruit | 3.83 cm | 2.65 cm | 3.19 cm |
| Berry length 2° fruit | 3.84 cm | 2.56 cm | 2.91 cm |
| Berry length 3° fruit | 3.62 cm | 3.39 cm | 2.88 cm |
| Ratio of primary fruit length to width | 1.98 | 1.55 | 1.62 |
| Shape description | Conic | Rough conic | Conic |
| Uniformity of berry shape | Excellent | Fair | Excellent |
| Color when full ripe | 203B | 203C | 203B |
| Number of drupelets per fruit | 147.67 | 59.00 | 75.83 |
| Drupelet weight | 5.10 mg | 9.30 mg | 7.90 mg |
| Individual seed weight | 3.95 mg | 3.95 mg | 3.95 mg |
| Glossiness | Medium glossy to dull | Medium glossy to dull | Medium glossy to dull |
| Firmness | Very good | Poor | Good |
| Flavor | Excellent | Excellent | Good |
| Texture of fruit when chewed | Very good to excellent | Excellent | Very good |

TABLE 7-continued

| Characteristic | Columbia Star | Marion | Black Diamond |
|---|---|---|---|
| Drupelet skin resistance to abrasion | Good | Poor | Good |
| Ease of separation of fruit from pedicel | Easy | Easy | Easy |
| Machine harvestability | Excellent | Excellent | Excellent |
| Resistance to heat damage of fruit | Medium to good | Low | Medium to good |
| Berries per inflorescence - mean | 7.00 | 7.20 | 11.50 |
| Berries per inflorescence range | 5-10 | 7-8 | 9-14 |
| Soluble solids (%; in Brix) | 12.80 | 12.28 | 10.47 |
| pH | 3.20 | 3.27 | 3.40 |
| Titratable acidity (% as citric acid) | 15.76 | 14.75 | 12.02 |
| Yield (actual kg · plt-1) | 6.98 | 5.83 | 4.75 |

COMPARISON WITH PARENTAL AND COMMERCIAL VARIETIES

'Columbia Star' differs from the female parent 'NZ 9629-1' (unpatented) in that 'Columbia Star' has medium-sized, glossy, large fruit (7-8 g), while 'NZ 9629-1' has slightly pubescent fruit that are smaller (4.5 g). Furthermore, while 'Columbia Star' has yields greater than 'Marion' (unpatented) 'NZ 9629-1' (unpatented) has yields comparable to 'Marion'

'Columbia Star' differs from the male parent blackberry plant 'ORUS 1350-2' (unpatented) in that it is 'Columbia Star' is spineless, has large (7-8 g), conic berries with excellent flavor, while 'ORUS 1350-1' (unpatented) is spiny, and has very large (10-12 g), barrel shaped berries with poor flavor.

'Columbia' Star differs from the commercial variety 'Marion' (unpatented) in that 'Columbia Star' is spineless and bears high yields of large, firm fruit, while 'Marion' is spiny, bears medium yields of medium sized, soft fruit. 'Columbia Star' differs from the commercial variety 'Black Diamond' (unpatented) in that 'Columbia Star' carries the 'Lincoln Logan' (unpatented) source of spinelessness and therefore the canes are completely spineless and the plants are vigorous with fruit that have excellent, aromatic flavor, while 'Black Diamond' (unpatented) carries the 'Austin Thornless' (unpatented) source of spinelessness and so has spines on the base of the canes and the plants are not vigorous and they produce fruit with a mild flavor.

I claim:

1. A new and distinct cultivar of blackberry plant, substantially as illustrated and described, characterized by its high yields of large, very uniformly shaped berries with very good flavor, sweetness, as characterized by soluble solids, pH, and titratable acidity that make them well suited for processing and that are borne on vigorous, completely thornless plants that can be harvested by machine.

* * * * *